(12) United States Patent
Falchuk et al.

(10) Patent No.: US 7,756,721 B1
(45) Date of Patent: *Jul. 13, 2010

(54) HEALTH CARE MANAGEMENT SYSTEM

(75) Inventors: Kenneth H. Falchuk, Newton, MA (US); Jose A. Halperin, Brookline, MA (US); Evan J. Falchuk, W. Newton, MA (US); Lawrence S. Brewster, E. Falmouth, MA (US)

(73) Assignee: Best Doctors, Inc., Boston, MA (US)

( * ) Notice: Subject to any disclaimer, the term of this patent is extended or adjusted under 35 U.S.C. 154(b) by 2546 days.

This patent is subject to a terminal disclaimer.

(21) Appl. No.: 09/705,198

(22) Filed: Nov. 2, 2000

Related U.S. Application Data

(63) Continuation-in-part of application No. 08/818,155, filed on Mar. 14, 1997, now Pat. No. 6,256,613.

(60) Provisional application No. 60/163,520, filed on Nov. 4, 1999.

(51) Int. Cl.
*G06Q 40/00* (2006.01)

(52) U.S. Cl. .............................................. 705/2; 705/3

(58) Field of Classification Search ................ 705/2, 705/3
See application file for complete search history.

(56) References Cited

U.S. PATENT DOCUMENTS

| 5,471,382 | A |   | 11/1995 | Tallman et al. ............... 364/406 |
| 5,619,991 | A |   | 4/1997  | Sloane ........................ 128/630 |
| 5,724,580 | A | * | 3/1998  | Levin et al. ............... 707/104.1 |
| 5,862,223 | A |   | 1/1999  | Walker et al. ................. 380/25 |
| 5,910,107 | A |   | 6/1999  | Iliff ........................... 600/300 |
| 5,946,659 | A |   | 8/1999  | Lancelot et al. ................. 705/3 |
| 6,014,631 | A |   | 1/2000  | Teagarden et al. .............. 705/3 |
| 6,047,259 | A |   | 4/2000  | Campbell et al. .............. 705/3 |

FOREIGN PATENT DOCUMENTS

| WO | 99/09506   | 2/1999 |
| WO | WO9909506  | 2/1999 |

OTHER PUBLICATIONS

Parsley, Martie Lynn, Ph.D., "Information needs, uses and information technologies in the living context of chronic illness: A participant observation study"; The Ohio State University, 1998, 255 pages.*
Bernard Dowling; "Effect of fundholding on waiting times: Database study"; British Medical Journal. (International edition). London: Aug 2, 1997. vol. 315, Iss. 7103; p. 290, 3 pgs.*
Steve Twedt; No new problems; Post-Gazette Staff Writer. Pittsburgh Post—Gazette. Pittsburgh, Pa.: Apr. 23, 1994. p. a.2.*
Coile, "E-Health: Reinventing Healthcare in the Information Age", Journal of Healthcare Management, vol. 45, No. 3, 206, May 2000.

* cited by examiner

*Primary Examiner*—Hani Kazimi
(74) *Attorney, Agent, or Firm*—Gordon E. Nelson; Patent GC LLC

(57) ABSTRACT

The present invention relates to a system and method for facilitating and managing health care between a medical provider and a patient. In one aspect, the system and method includes providing a patient having a first criteria, which includes a medical symptom. The system and method also include selecting a subset of medical providers having expertise in treating the medical symptom, generating a care request to obtain a treatment proposal for the medical symptom of the patient, and updating the care request with medical information associated with the medical symptom. The system and method further include receiving at least one treatment proposal of the medical symptom from the medical providers and selecting a treatment proposal of the medical symptom from the medical providers.

20 Claims, 15 Drawing Sheets submit a care request

Care Requestor Information All fields below are required

| | |
|---:|---|
| Name | ──402(a) |
| Title | ──402(b) |
| Organization | ──402(c) |
| Street address | ──402(d) |
| Address (cont.) | ──402(e) |
| City | ──402(f) |
| State/Province | ──402(g) |
| Zip/Postal code | ──402(h) |
| Country | ──402(i) |
| Work Phone | ──402(j) |
| FAX | ──402(k) |
| E-mail | ──402(l) |
| URL | ──402(m) |

Patient Information All fields below are required

Name [ ] — 404(a)
Date of birth [ ] -mm/dd/yy — 404(b)
Sex [ ] — 404(c)
Email [ ] — 404(d)
Patient's diagnosis [ ] — 404(e)
ICD9 code [ ] — 404(f)

Description of treatment requested:

[ ] — 406

CPT code(s): [ ] — 408

Medical summary:

[ ] — 410

Other medical problems:

[ ] — 412

Date preference for receiving care: [ ] -mm/dd/yy — 414

Is the patient willing to go out of state to receive care?

Other preferences (e.g., private room, vegetarian meals, etc.):

[ ] — 416

---

Insurance Information  All fields below are required

FIG. 4B

Name of medical insurance policy [_____] — 418

Medical policy # [_____] — 420

Decribe the medical coverage for this treatment:

[_____] — 422

Limitations of the coverage for this treatment:

[_____] — 424

Exclusions relevant to the coverage for this treatment:

[_____] — 426

Submit Care Request

I have read and understand the rules and conditions.
By clicking "yes", I indicate my acceptance of these rules.

Yes ⎫
No  ⎭ — 428

Your name: [_____] — 430

[ Submit Form ]  [ Reset Form ]   FIG. 4C

Medical Summary

REF: — 410

48 year old male patient with weakness in the right arm and face. Functional MRI demonstrates lesion in the left parietal love, abutting motor area and speech area of the cortex

FIG. 4D

Treatment Proposal

| | | |
|---|---|---|
| 502(a) | Case# | |
| 502(b) | Payer organization | |
| 502(c) | Patient name | |
| 502(d) | Patient DOB | Patient sex |

| | | |
|---|---|---|
| | General Information | |
| 504(a) | Proposing hospital or medical expert | |
| 504(b) | Proposal submitted by -Name | |
| 504(c) | -Title | |
| 504(d) | Hospital at which patient will be treated | |
| 504(e) | City, state | |
| | Principle Physician Profile | |
| 506(a) | Name | |
| 506(b) | Title | |
| 506(c) | Age | |
| 506(d) | Sex | |
| 506(e) | Years in practice | |
| 506(f) | Board certifications | |
| 506(g) | Awards and recognitions | |
| 506(h) | Publications | |
| | Care Plan | |
| 508(a) | Detailed description of the proposed treatment | |

FIG. 5A

Treatment Proposal

| | | |
|---|---|---|
| 508(b) | Treatment plan is: | |
| 508(c) | # of times the physician in charge has performed the treatment in the past 12 months | |
| 508(d) | # of times the hospital has performed the treatment in the past 12 months | |
| 508(e) | Complication rates and types of complications for this treatment at the hospital | |
| 508(f) | Survival rate for this treatment at the hospital | |
| 508(g) | Describe any medical care the patient should undergo prior to admission | |
| | Pre-admission | |
| 510(a) | Will the hospital handle all pre-admission arrangements related to this Care Proposal? | |
| 510(b) | If no, indicate additional information the patient must supply for pre-admission | |
| | In-hospital Care | |
| 512(a) | Hospital's preferred date of admission | |
| 512(b) | Date treatment will begin | |
| 512(c) | Expected length of stay | |
| 512(d) | Ratio of patients per nurse on the patient's floor during the acute, post-procedure period | |
| 512(e) | Location of patient during this period | |
| | Support Team | |
| 514(a) | Anesthesiology | |
| 514(b) | Pathology | |

FIG. 5B

Treatment Proposal

| | |
|---|---|
| 514(c) — Radiology | |
| 514(d) — Rehabilitation/PT | |
| 514(e) — Other | |

Post Discharge

| | |
|---|---|
| 516(a) — Describe the medical care required following discharge including follow-up visits | |
| 516(b) — To what extent must follow-up care be handled at the proposing hospital? Why? | |
| 516(c) — Describe how the physician in charge will coordinate care with a physician in the patient's local area | |

Additional Considerations

| | |
|---|---|
| 518 — Note any additional considerations here | |

Financial Proposal

| | |
|---|---|
| 520(a) — Pre-admission costs | |

FIG. 5C

Treatment Proposal

| | |
|---|---|
| | In-hospital costs — 520(b) |
| | Post-discharge costs — 520(c) |
| | Total proposed price — 520(d) |
| | Special payment terms that apply — 520(e) |

FIG. 5D

Case #: 27  
Payer code

Diagnosis  
Treatment requested

Treatment Proposal - Data

| | Treatment Proposal 1 | Treatment Proposal 2 |
|---|---|---|
| 508(a) – Detailed description of the proposed treatment | | |
| 508(b) – Treatment plan is: | | |
| 508(c) – # of times the physician in charge has performed the treatment in the past 12 months | | |
| 508(d) – # of times the hospital has performed the treatment in the past 12 months | | |
| 508(g) – Describe any medical care the patient should undergo prior to admission | | |
| 510(a) – Will the hospital handle all pre-admission arrangements related to this treatment proposal? | | |
| 512(c) – Expected length of stay | | |
| 516(a) – Describe the medical care required following discharge, including follow-up visits | | |
| 516(b) – To what extent must follow-up care be | | |

FIG. 6A

| Treatment Proposal - Data | |
|---|---|
| 516(b) (continued) — handled at the proposing hospital? Why? | |
| 516(c) — Describe how the physician in charge will coordinate care with a physician in the patient's local area | |
| 520(d) — Total proposed price | |
| 520(e) — Special payment terms that apply | |

| Comparative Report<br>Payer code | Diagnosis<br>Treatment requested<br>602<br>Treatment Proposal 3 | Treatment Proposal<br>604<br>Treatment Proposal 4 |
|---|---|---|
| 508(a) — Detailed description of the proposed treatment | | |
| 508(b) — Treatment plan is: | | |
| 508(c) — # of times the physician in charge has performed the treatment in the past 12 months | | |
| 508(d) — # of times the hospital has performed the treatment in the past 12 months | | |
| 508(g) — Describe any medical care the patient should undergo prior to admission | | |
| 510(a) — Will the hospital handle all pre-admission arrangements related to this Care proposal? | | |
| 512(c) — Expected length of stay | | |
| 516(a) — Describe the medical care required following discharge, including follow-up visits | | |
| 516(b) — To what extent must follow-up care be handled at the proposing hospital? Why? | | |
| 516(c) — Describe how the physician in charge will coordinate care with a physician | | |

| | | Treatment Proposal - Data |
|---|---|---|
| 516(c) (continued) — in the patient's local area | | |
| 520(d) — Total proposed price | | |
| 520(e) — Special payment terms that apply | | |

FIG. 6D

HEALTH CARE MANAGEMENT SYSTEM

RELATED APPLICATIONS

This application claims priority to U.S. Provisional Application Ser. No. 60/163,520, filed on Nov. 4, 1999 and a continuation-in-part application of U.S. patent application Ser. No. 08/818,155, filed on Mar. 14, 1997.

FIELD OF THE INVENTION

The invention relates generally to a health care management system and more particularly to a system for facilitating and managing health care between a medical provider and a patient.

BACKGROUND OF THE INVENTION

In the United States alone, approximately 4.5 million complex surgeries are performed annually. This estimate is expected to increase over time. Patients having a medical symptom that necessitates a complex treatment (i.e., surgery) are typically limited by the medical providers (e.g., hospitals and medical specialists) included in the payer's (e.g., insurance company) plan or network. Furthermore, medical providers included in the payer's plan or network may not be specialized in complex treatments. Payers also often attempt to offer "out-of-network" coverage, but are frequently unable to manage the resulting monetary expenditures. Due to the frequent improper management of the resulting monetary expenditures, payers can deny the patient access to the "out-of-network" medical provider or place a significant supplemental cost burden on the patient.

Additionally, due to the complexity and variety of medical symptoms that compel a complex treatment, each medical case involving a patient having such a medical symptom is somewhat unique. Therefore, although a medical provider in the payer's network can be specialized in performing a certain complex treatment, the patient having the medical symptom may require a different medical provider that is focused on a subset of a specialty of medicine. In general, the patient does not know of the medical providers that specifically specialize in the patient's medical symptom. Even if known, the patient typically cannot learn about the quality of care that these specialized medical providers have supplied to patients in similar situations. The patient does not frequently have information to enable a comparison between two or more medical providers. Moreover, besides a primary care physician's referral, when patients need a complex treatment, patients often seek alternative sources of reliable information to help them identify the most qualified medical provider and best course of action. The patient does not generally have broad access to expert medical providers and information on these expert medical providers located in various parts of the country or in other countries.

Thus, there exists a need to enable patients to attain information about and to have access to a broad range of medical providers.

SUMMARY OF THE INVENTION

The present invention relates to a method for facilitating and managing health care between a medical provider and a patient. The present invention facilitates communications between a patient having a medical symptom and medical providers having expertise in treating the medical symptom of the patient. Further, the patient communicates with the medical providers and obtains a treatment proposal for the medical symptom in a reduced period of time. The present invention facilitates the patient receiving medical information on the medical providers that supply a treatment proposal for the medical symptom. Moreover, the patient receives a comparative report enabling the comparison of information, such as cost and quality of service, about medical providers.

In one aspect, the invention includes a method for managing health care. The method includes providing a patient having a first criteria, which includes a medical symptom. The method also includes selecting a subset of medical providers having expertise in treating the medical symptom, generating a care request to obtain a treatment proposal for the medical symptom of the patient, and updating the care request with medical information associated with the medical symptom. The method further includes receiving at least one treatment proposal of the medical symptom from the medical providers and selecting a treatment proposal of the medical symptom from the medical providers. In one embodiment, the method additionally includes transmitting each treatment proposal to each medical provider, receiving a treatment proposal from each medical provider, and transmitting each treatment proposal to the patient. In one embodiment, the method includes receiving a treatment proposal that is modified after transmitting each treatment proposal to each medical provider.

In another aspect, the invention includes a patient-client interface for providing a patient having a medical symptom, a provider-client interface for providing a medical provider having expertise in treating the medical symptom, and a server in communication with the provider-client interface for receiving treatment proposal of the medical symptom. The server is also in communication with the patient-client interface for receiving a care request corresponding to the medical symptom. The server communicates the treatment proposal to the patient-client interface and receives a selection of a treatment proposal from the patient-client interface.

In yet another aspect, the invention includes a method of consulting a medical specialist. The method includes receiving a consultation request from a treating physician via a telecommunications system. The consultation request requests a specialist to be consulted. Additionally, the method includes retrieving medical information relevant to but independent from the consultation request from an information database accessible by a computer. The relevant medical information is retrieved by a medical information expert. The method also includes the steps of providing the relevant medical information and the consultation request to the medical specialist via the telecommunications system and receiving a comment made by a medical specialist in response to the consultation request and the relevant medical information. Additionally, one or more comments are provided to the treating physician. Further, a continuing medical education credit for the treating physician is provided.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIGS. 4A, 4B, 4C, and 4D illustrate an exemplary embodiment of a care request according to the present invention.

FIGS. 5A, 5B, 5C, and 5D illustrate an exemplary embodiment of a treatment proposal according to the present invention.

FIGS. 6A, 6B, 6C, and 6D illustrate an exemplary embodiment of a comparative report according to the present invention.

DETAILED DESCRIPTION

Figure 1:
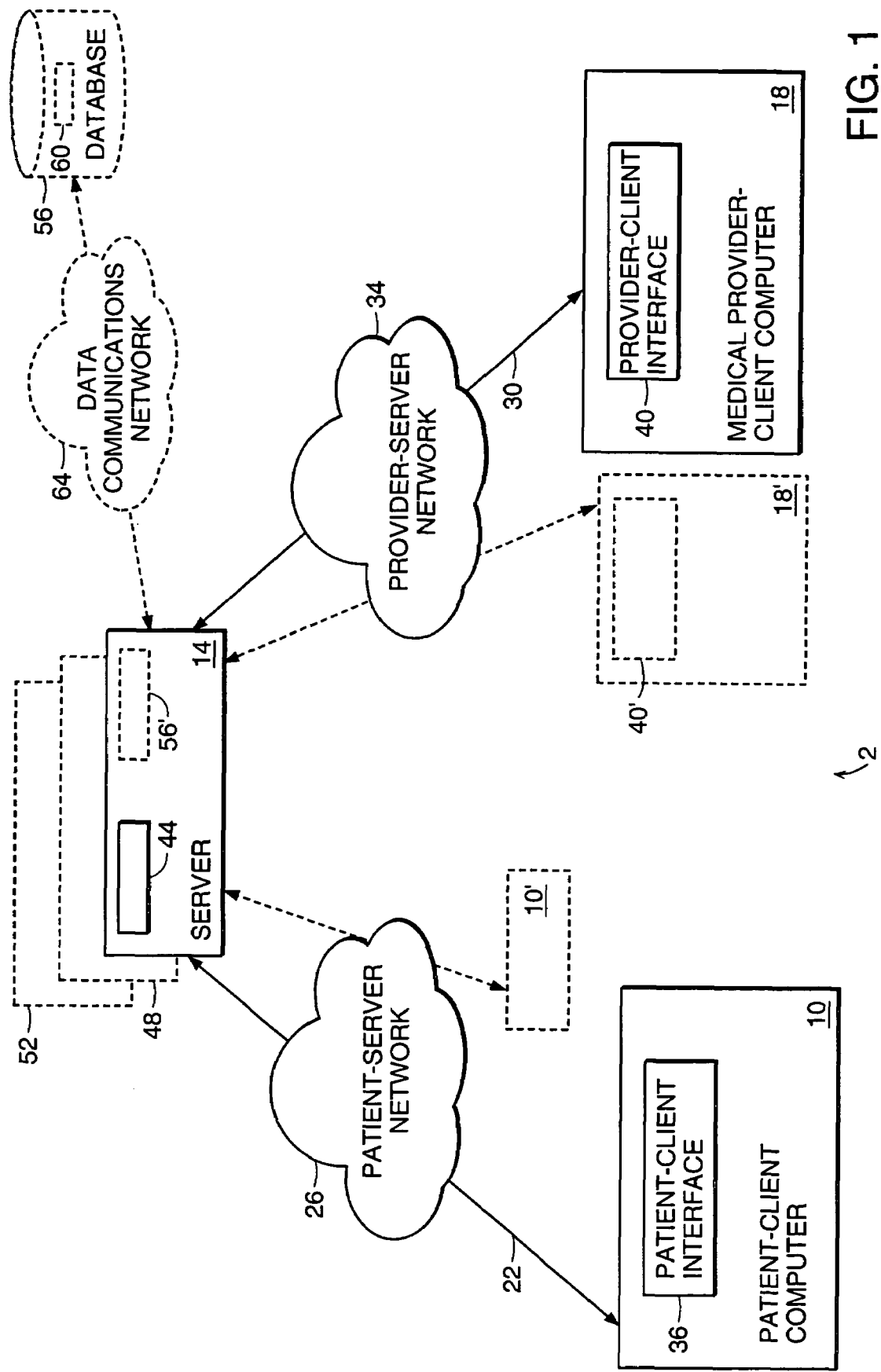
FIG. 1 illustrates a block diagram of an embodiment of a health care management system according to the present invention.

FIG. 1 illustrates a block diagram of an embodiment of a health care management system 2 that includes a patient-client computer 10, or patient-client, a server 14, and a medical provider-client computer 18, or provider-client. The patient-client 10 is in communication with the server 14 over a patient communication path 22 and passes through a patient-server network 26. The server 14 is also in communication with the provider-client 18 over a provider communication path 30 and passes through a provider-server network 34. It should be noted that FIG. 1 is an exemplary embodiment intended only to illustrate, and not limit, the invention.

The patient-server network 26 and the provider-server network 34 are large scale communication networks and can be a local-area network (LAN), a medium-area network (MAN), or a wide area network (WAN) such as the Internet or the World Wide Web (i.e., web). In one embodiment, the patient-server network 26 (e.g., the patient communication path 22) supports secure communications. In a further embodiment, communications occur after the user's password is verified by the server 14. In one embodiment, the provider-server network 34 (e.g., the provider communication path 30) is a protected network that is physically secure from public access. In another embodiment, because the provider-server network 34 is not a publicly available network, the provider-server network 34 is a non-secure network (i.e., the provider communication path 30 is a non-secure communication path). Example embodiments of the communication paths 22, 30 include standard telephone lines, LAN or WAN links (e.g., T1, T3, 56 kb, X.25), broadband connections (ISDN, Frame Relay, ATM), and wireless connections. The connections over the communication paths 22, 30 can be established using a variety of communication protocols (e.g., TCP/IP, IPX, SPX, NetBIOS, Ethernet, RS232, and direct asynchronous connections).

The patient-client 10 and the provider-client 18 can be any personal computer (e.g., 286, 386, 486, Pentium, Pentium II, Macintosh computer), Windows-based terminal, Network Computer, wireless device, information appliance, RISC Power PC, X-device, workstation, mini computer, main frame computer, personal digital assistant, or other computing device that has a windows-based desktop and sufficient persistent storage for executing a small, display presentation program. Windows-oriented platforms supported by the patient-client 10 and the provider-client 18 can include, without limitation, WINDOWS 3.x, WINDOWS 95, WINDOWS 98, WINDOWS NT 3.51, WINDOWS NT 4.0, WINDOWS 2000, WINDOWS CE, MAC/OS, Java, and UNIX. The client 10 can include a visual display device (e.g., a computer monitor), a data entry device (e.g., a keyboard), persistent or volatile storage (e.g., computer memory) for storing downloaded application programs, a processor, and a mouse.

The patient-client 10 includes a patient-client interface 36 and the provider-client 18 includes a medical provider-client interface 40. The interfaces 36, 40 can be text driven (e.g., DOS) or graphically driven (e.g., Windows). In one embodiment, the patient-client interface 36 is a web browser, such as Internet Explorer developed by Microsoft Corporation in Redmond, Wash., to connect to the patient-server network 26. In a further embodiment, the web browser uses the existing Secure Socket Layer (SSL) support, developed by Netscape in Mountain View, Calif., to establish the patient-server network 26 as a secure network.

As described more fully below, a patient having a first criteria, including a medical symptom, employs the patient-client interface 36 on the patient-client 10 to obtain treatment for the medical symptom. In another embodiment, an employer group uses the patient-client interface 36 to communicate with the server 14 to enable treatment for the patient's medical symptom. Alternatively, a payer organization uses the patient-client interface 36 to communicate with the server 14. Example embodiments of a payer organization include, but are not limited to, insurance companies and HMO's.

Similar to the clients 10, 18, the server 14 can be any personal computer described above. In one embodiment, the server 14 hosts one or more software modules 44 that the patient-client 10 and/or the provider-client 18 can access. In another embodiment, the server 14 is a member of a server farm, which is a logical group of one or more servers that are administered as a single entity. In the embodiment shown, the server farm includes the server 14, a second server 48, and a third server 52.

As described more fully below, a medical provider having expertise in treating the medical symptom of the patient employs the provider-client interface 40 to propose a treatment for the symptom of the patient. Examples of the medical provider include, but are not limited to, medical physicians, medically trained individuals, hospitals, medical specialists, medical experts, other facilities providing medical treatment, and the like.

In one embodiment, the server 14 is also in communication with a database 56. The database 56 is a server that stores and manages data. The server 14 accesses the information stored on the database 56 by interfacing with a database module 60. In one embodiment, the database module 60 maintains the server 14 data in a Lightweight Directory Access Protocol (LDAP) data model. In other embodiments, the database module 60 stores data in an ODBC-compliant database. For example, the database module 60 can be provided as an ORACLE database, manufactured by Oracle Corporation of Redwood Shores, California. In other embodiments, the database module 60 can be a Microsoft ACCESS database or a Microsoft SQL server database. The database 56 retrieves data from local memory and transmits the data to the server 14 over a data communications network 64. In another embodiment, a database 56' is located on the server 14.

In a further embodiment, a second medical provider-client computer 18' having a second medical provider-client interface 40' communicates with the server 14 through the provider-server network 34. A second medical provider, such as a second hospital, can propose a second treatment for the medical symptom of the patient.

Figure 2:
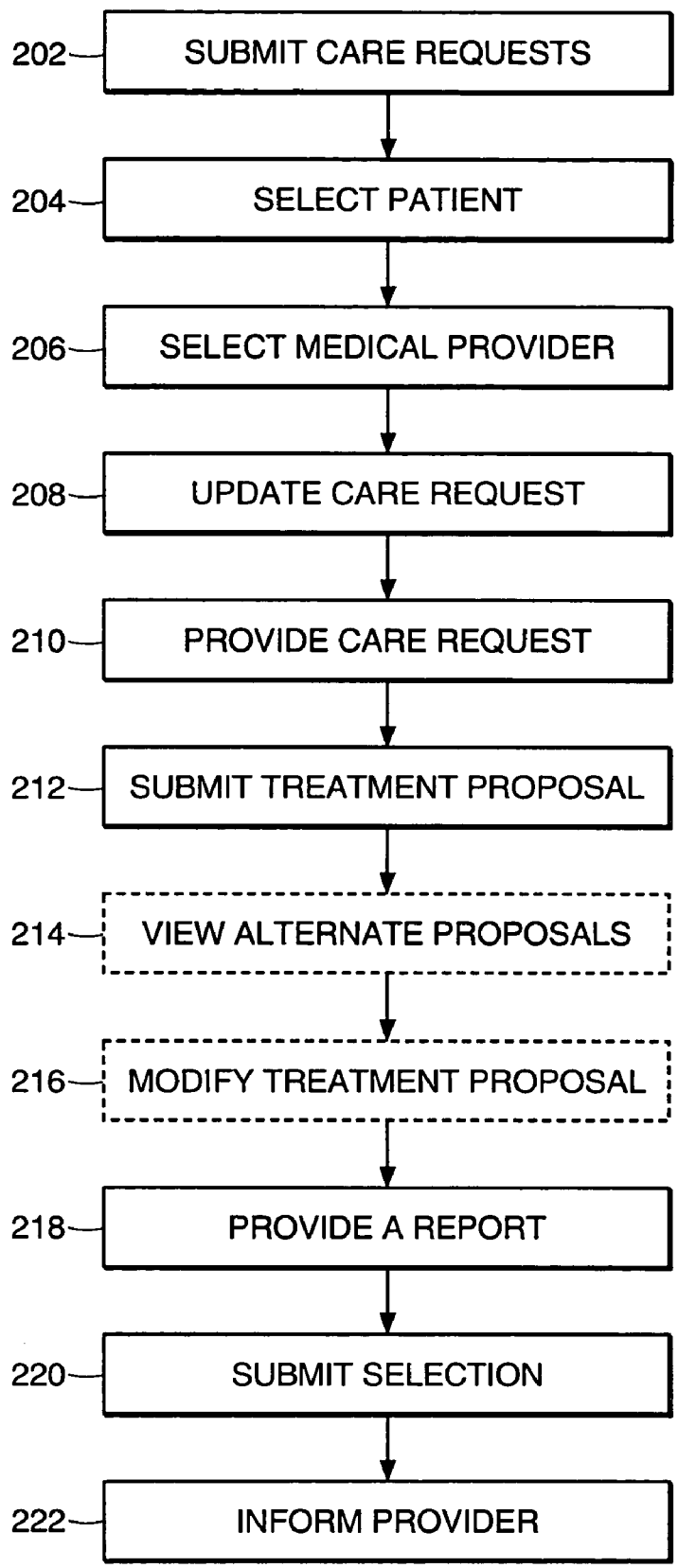
FIG. 2 illustrates a flow diagram of an embodiment of the steps performed by the health care management system according to the present invention.

FIG. 2 illustrates a flow diagram of an embodiment of the steps performed by the health care management system 2 according to the present invention. Patients use the patient-client interface 36 to submit (step 202) a care request (i.e., a request for treatment) to the server 14 over the patient communication path 22. The software module 44 executing on the server 14 then selects (step 204) one of the patients having a first criteria. The first criteria includes a medical symptom of the patient. Additional examples of the first criteria include, without limitation, insurance coverage of the patient, other means of payment, and a certain level of complexity required to treat the medical symptom.

The software module 44 selects (step 206) a subset of medical providers that have expertise in treating the medical symptom. For example, the software module 44 selects the subset of medical providers based on, but not limited to, the previous cost of treating an identical or similar medical symptom, the medical experience in the area related to the medical symptom (e.g., time working in the area related to the medical symptom), the number of procedures treating the medical symptom that have been performed by the medical provider, the amount of education received, the reputation of the medical provider, and the like. In one embodiment, the server 14 retrieves from the database 56 (using the database module 60) medical information associated with a group of medical providers to assist in the determination of the subset of medical providers that have expertise in treating the medical symptom. In another embodiment, a staff physician, or medically trained individual, that is independent from the medical providers selects the subset of medical providers that have expertise in treating the medical symptom.

Although described above with multiple patients submitting care requests, one patient can submit a care request to the server 14. In this embodiment, the software module 44 continues to determine if the patient is accepted based on the determination of the patient having the first criteria (e.g., insurance coverage).

In one embodiment, staff physicians use the server 14 to update (step 208) the care request with medical information associated with the medical symptom of the patient. The staff physician uses the server 14 to research the medical symptom before updating the care request. The database 56 provides the server 14 with relevant articles and other information on the medical symptom that the staff physician uses to update the care request. Once the care request is complete, the server 14 provides the care request to the provider-clients 18, 18' over the provider-server network 34. Although described below with two provider-clients 18, 18', the invention functions properly when the server 14 provides the care request to the single provider-client 18.

Each medical provider reviews the care request and determines a treatment proposal, as described further below, to treat the medical symptom of the patient. For example, each medical provider determines its treatment proposal by examining the difficulty associated with treating the medical symptom, the familiarity with treating the medical symptom, and the availability of the correct medical specialists. The medical providers then transmit (step 212) their treatment proposals to the server 14 over the provider-server network 34.

In one embodiment, the software module 44 (or the staff physician) prepares a preliminary comparative report of the received treatment proposals. The report lists the treatment proposals submitted in step 212 and facilitates comparisons between the two treatment proposals. The software module 44 then transmits the report to both provider-clients 18 and 18', thereby enabling each medical provider to view (step 214) the other treatment proposals submitted by the other medical providers. The medical provider can compare its treatment proposal with the other treatment proposals and can modify (step 216) its treatment proposal after viewing the other proposals. For example, if the patient requests treatment for a liver transplant, a first medical provider can interpret the question (on the treatment proposal) about the number of times that a liver transplant has been performed at that medical provider to mean a transplant on a living person and a second medical provider can interpret the question as a number representing the total number of liver transplants performed (i.e., cadaveric and living liver transplants). More specifically, if the treatment proposal submitted by the first medical provider states that the medical provider has performed liver transplants on 10 people over the past year and a second treatment proposal submitted by the second medical provider states that the medical provider has performed cadaveric and living liver transplants 150 times this year, the first medical provider reviews the second medical provider's treatment proposal and can change their number of liver transplants performed to accurately reflect the total number of transplants performed in the year. The viewing (step 214) and modifying (step 216) of treatment proposals can occur several times. This process of multiple views and modifications of the treatment proposal benefits both the patient and the medical providers. More specifically, the patients benefit because they obtain treatment proposals that accurately reflect the services of the medical providers. Further, the medical providers benefit because they can correct mistakes and inaccurate portrayals of their services. In one embodiment, the software module 44 on the server provides the provider-clients 18, 18' with a date on which no further changes to the treatment proposals can occur. Upon this date, the medical providers submit final treatment proposals to the server 14.

Once the final treatment proposals are submitted, the staff physician and/or the software module 44 generates a final comparative report that includes each treatment proposal and provides (step 218) the final comparative report to the patient via the patient-client interface 36. In one embodiment, the staff physician recommends a treatment proposal submitted by one of the medical providers that the staff physician considers to meet the patient's interests. Examples of factors that can affect the staff physician's recommendation include, without limitation, the quality of service of the medical provider, cost of the medical provider, experience of the medical provider, and travel expenses for the patient to arrive at the medical provider. The patient then submits (step 220) its selection of a treatment proposal to the server 14 over the patient-server network 26. The server 14 consequently informs the medical provider that submitted the selected treatment proposal of the patient's acceptance through a message to the provider-client interface 40 (or 40'). In one embodiment, the server 14 transmits an email message to the provider-client 18 to denote acceptance. However, any other communication between the medical provider and the staff physician indicating the patient's acceptance to the treatment proposal is sufficient.

Figure 3:
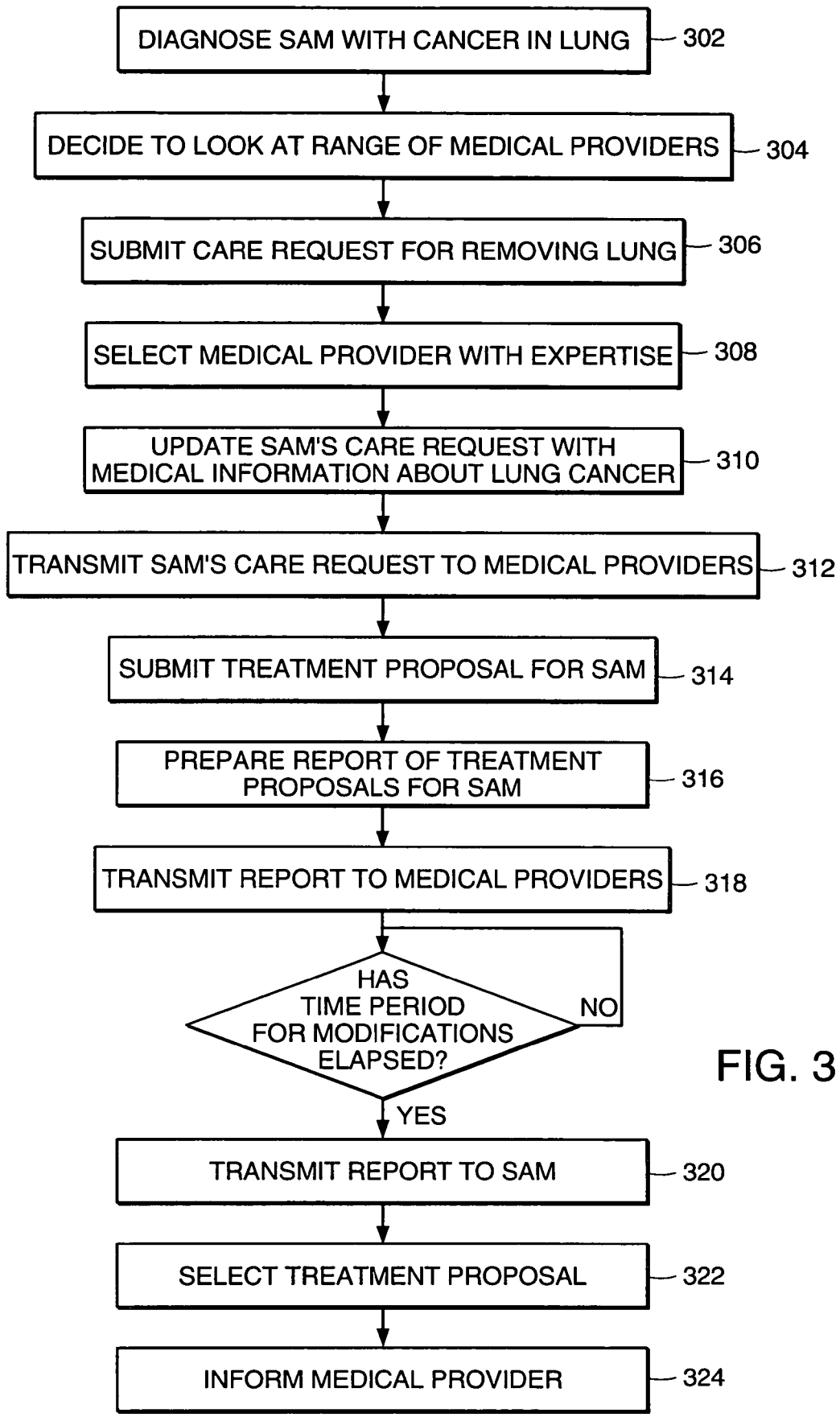
FIG. 3 illustrates an exemplary embodiment of the present invention.

FIG. 3 is an illustrative example of the present invention. Sam, a patient, is diagnosed (step 302) with a solitary cancer nodule in his left lung. He also has a significant history of coronary artery disease with angina, which is a condition in which spasmodic attacks of suffocating pain occur. After weighing his choices, Sam determines that he should undergo surgery with a team of cardiac and thoracic surgeons to perform a coronary by-pass and remove the lung. Sam's primary care physician (i.e., which is member of his medical insurance network) referred him to a hospital with a good local reputation. However, Sam's particular case is complex and risky, and Sam determines (step 304) that he should look at a range of medical providers (i.e., "out-of-network" medical providers).

Sam uses a user interface (i.e., the patient-client interface 36) which, in one embodiment is executing on his computer (i.e., patient-client 10), to submit (step 306) a care request. After Sam's submission, the server 14 and/or the independent staff physician selects (step 308) a subset of medical providers having expertise in treating a solitary cancer nodule in a patient's left lung while having a history of coronary artery disease with angina (i.e., expertise in performing a coronary by-pass and removing the left lung). After the server 14 selects the medical providers, the staff physician updates (step 310) the care request with additional medical information. The staff physician then transmits (step 312) Sam's care request to these medical providers. The selected medical providers each review Sam's care request and submit (step 314) a treatment proposal to perform Sam's surgeries. The server 14 prepares (step 316) a comparative report of the treatment proposals and transmits (step 318) the report to the medical providers for review and/or modifications of their respective treatment proposals. Once the time period for modifications elapses, the server 14 prepares a final comparative report of the treatment proposals and transmits (step 320) this report to Sam. Sam reviews the report and selects (step 322) one of the treatment proposals. The server 14 consequently informs (step 324) the medical provider that submitted the selected treatment proposal of Sam's acceptance.

Figure 4A:
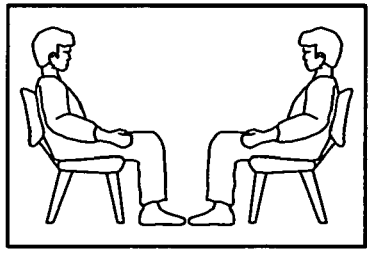

Referring to FIGS. 4A, 4B, 4C, and 4D, an example of a care request is shown. A payer of the treatment that the patient requests, such as the insurance company that provides coverage to the patient, provides general payer information elements 402(a)-402(m). In another embodiment, the patient provides the general payer information elements 402(a)-402(m). The patient then provides general patient information elements 404(a)-404(f) and a description of treatment requested 406. Further, the patient (or payer) provides Current Procedure Terminology, or CPT, codes 408. CPT is an accepted listing of descriptive terms and identifying codes for reporting medical services under public and private health insurance programs. The patient can also provide a medical summary 410, and other medical problems 412. In another embodiment, a staff physician provides the medical summary 410 of the medical symptom of the patient, as illustrated in FIG. 4D.

Referring to FIGS. 5A, 5B, 5C, and 5D, an example of a treatment proposal 500 that a medical provider submits to the server 14 is shown. Information identifying the care request (i.e., a case number) and the medical provider is denoted by the identifying information elements 502(a)-502(d). General information regarding the medical provider, such as the city of the hospital, is denoted by provider information elements 504(a)-504(e). General information of the principle medical expert, such as the number of years in practice, is denoted by the medical expert information elements 506(a)-506(h).

The treatment proposal 500 further includes a care plan 508. An embodiment of the care plan is illustrated with care information elements 508(a) through 508(g) and can include information such as a detailed description 508(a) of the proposed treatment. The treatment proposal 500 includes pre-admission information elements 510(a)-510(b) to describe additional information that is required for pre-admission of the patient. Additionally, the treatment proposal 500 contains further information such as, but not limited to, in-hospital care information elements 512(a)-512(e), support team information elements 514(a)-514(e), post-discharge information elements 516(a)-516(c), additional considerations 518, and financial proposal information elements 520(a)-520(e).

FIGS. 6A, 6B, 6C, and 6D illustrate an embodiment of an example of a comparative report 600. The comparative report 600 facilitates the comparison between the information included in a first treatment proposal 602 and a second treatment proposal 604. The comparative report 600 includes several of the information elements included in the treatment proposal 500 shown in FIGS. 5A, 5B, 5C, and 5D, such as the detailed description 508(a) of the proposed treatment and the total proposed price 520(d).

Figure 7:
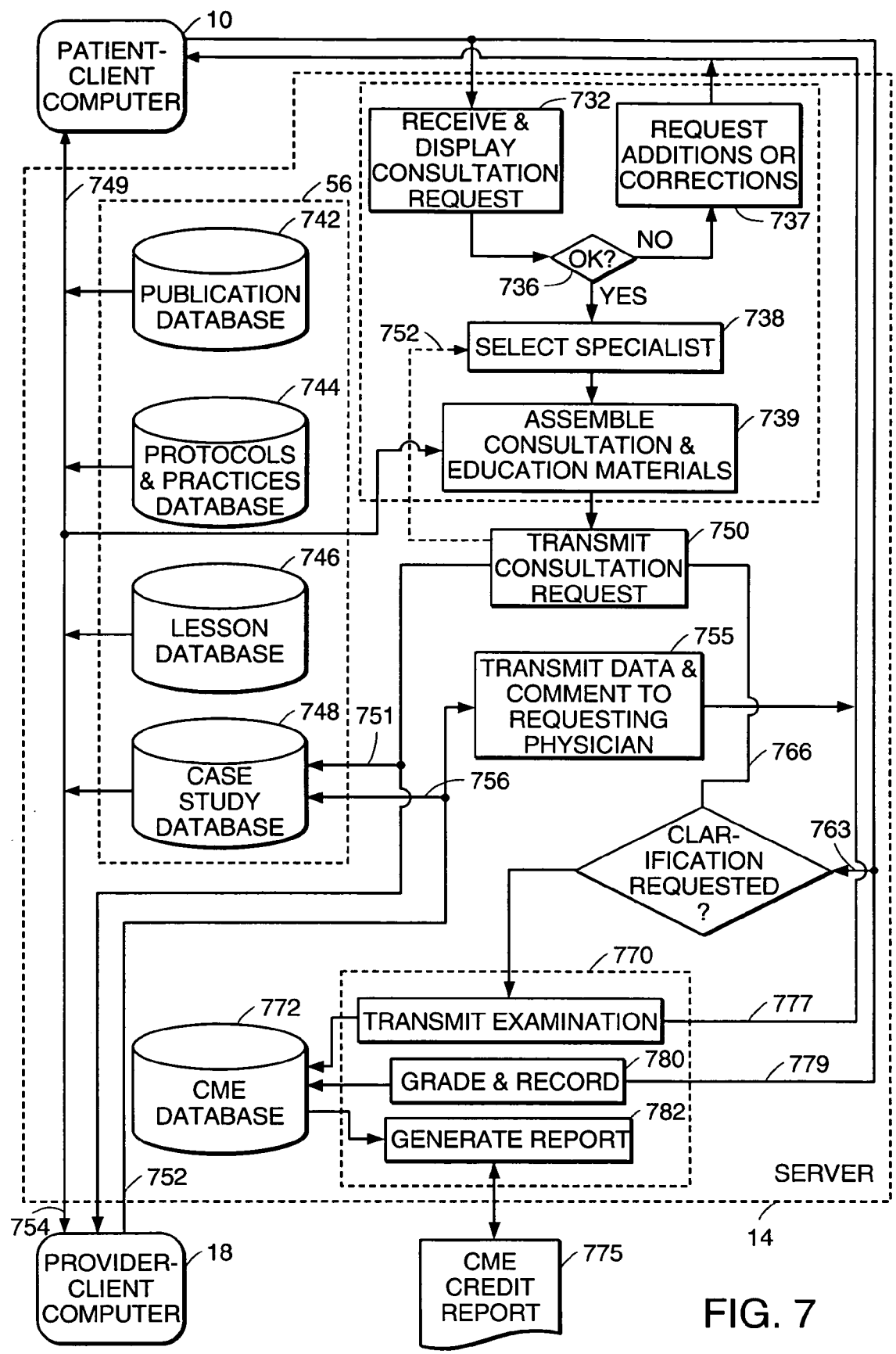
FIG. 7 illustrates a data flow diagram depicting the principle functions performed by a server during processing and management of a consultation session between a primary care physician and a selected medical provider.

FIG. 7 illustrates a data flow diagram depicting an embodiment of functions performed by the patient-client 10 during processing and management of a consultation session between a primary care physician and a medical provider. In this embodiment, a medical physician utilizes the patient-client 10 to formulate and transmit a request for consultation to the server 14. The server 14 processes and relays the request to the provider-client 18. The server 14 receives the request for consultation and displays information contained in the request for initial review by the staff physician, as indicated at 732. Programmatic tests are performed by the patient-client 10 and/or the server 14 to test the validity of the data entered into the formatted fields of the consultation request. Consequently, the staff physician need only review the request to insure that its content is adequate to enable the selection of one or more medical providers having expertise in the specialty in which consultation is sought. If the content is deficient, the staff physician notes the deficiency in a rejection message returned to the requesting physician as indicated at 736 and 737 in FIG. 7.

The staff physician then selects a medical provider to handle the request as indicated at 738 and forwards the request to the selected medical provider together with selected materials which are obtained and assembled at 739 from the database 56' which stores medical information which can be relevant to the request.

This database 56' advantageously includes a publication database module 742 consisting of abstracts or the full text of articles in medical journals, either stored locally in the server's processor's mass storage facility, or in an available medical database 60 (not shown), such as Medline/Medlars, connected to the server 14 over the data communications network 64 (not shown). In addition, the database 56' further advantageously contains a tutorial database module 744 containing background lessons which are selectively made available to the requesting physician as an adjunct to, and in support of, the comments to be received from the information assembled at 739 in support of the request. The case study database module 748 stores this information in a case history file for this consultation, as indicated at 751. Further information is thereafter added to this case history file as the consultation proceeds. The server 14 advantageously stores the request for consultation in the case history file in the form of a summary document expressed in hypertext markup language (HTML) which incorporates links to other HTML documents and/or supporting materials from the information database module 740. The consultation request can then be reviewed by the selected medical provider using a hypertext document browser, which retrieves and displays selected linked HTML documents and linked files as needed directly from the information database 740.

To insure that the request for consultation is handled in a timely fashion by the selected medical provider, the staff physician or other supervisory personnel is notified, as indicated at 752, in the event that an acknowledgment is not received from the provider-client 18 within a predetermined duration. In the absence of an indication that the request for consultation has been received and is being handled, delay notification 752 permits the staff physician to select a different available medical provider to handle the request in timely fashion when necessary.

Using the facilities provided by the provider-client 18, the selected provider enters a text comment answering the consultation report to form information structure comment information, which can include reference to supporting articles, lessons, protocols, or prior case studies in the information database module 740. As indicated at 754, the provider can make independent search requests to the database 56' to obtain information in aid of the consultation, so that the citations supplied by the consulting medical provider can include not only those materials identified by the automated searches performed by the staff physician but also supplemental materials newly cited by the medical provider. Moreover, the provider can append any other data which is available to the structured comment information, including image data or materials available to the medical provider from another database (not shown).

The structured comment information from the consulting medical provider is then returned to the server 14 which forwards the comment information to the patient-client computer 10 as indicated at 755. In addition, the server 14 also stores the responsive comment in the case study database module 748 for inclusion in the case history file established at 751 to hold the original consultation request, as indicated at 756.

The requesting primary care physician is accordingly supplied with the advisory comments of the consulting provider and a body of documented supporting materials, which can include relevant published articles from publication database module 742, documented practices and protocols from database module 744, tutorial lessons material from the database module 746, and prior relevant case histories from the case study database module 748. The response to the consultation request which is supplied to the physician also advantageously takes the form of a summary document expressed in HTML and includes links to supporting HTML documents and retrieval supporting documents supplied by the medical provider. Using an HTML browser, the requesting primary care physician can, accordingly, review the provider's comments and the supporting documentation using the HTML browsing facilities of the patient-client 10.

Although the initial comment and documentation supplied by the medical provider can in many cases wholly satisfy the needs of the requesting primary care physician, clarification can be requested when needed. The clarification request message is transmitted to the server 14 from the patient-client 10 and received as indicated at 763. The incoming message is examined at 765 to determine whether a clarification is requested or, in the alternative, that the requesting physician wishes to conclude the consultation. If the received message is a request for clarification, it is transmitted to the medical provider for further comment as indicated at 766; otherwise, a continuing education (CME) accreditation module indicated generally at 770 is notified that the consultation has been successfully concluded. The accreditation module 770 administers a CME database module 772 which records information concerning the consultation sessions and produces accreditation reports 775 which can be submitted to the responsible accreditation authority to certify that the requesting physician is entitled to CME credits based on his or her participation in the consultation session. When required for credit, the requesting physician can also be requested to complete an examination form testing the knowledge gained, in which case an examination is made available to the requesting physician as indicated at 777. This examination form can also be advantageously implemented by an HTML form which is transmitted to the requesting physician, completed, and resubmitted to the server 14 as indicated at 779. The completed examination form is then graded and the results posted to the CME database module 772 as indicated at 780. The credits accumulated by individual primary care physicians who have participated in learning sessions are then detailed in the CME credit report 775 which is thereafter produced for submission to the responsible accrediting body as indicated at 782.

While the invention has been particularly shown and described with reference to specific preferred embodiments, it should be understood by those skilled in the art that various changes in form and detail can be made therein without departing from the spirit and scope of the invention as defined by the appended claims.

What is claimed is:

1. A method of managing a health care request for a patient, the health care request having a first criteria that is a medical symptom of the patient, the health care request being made to an intermediary between a source of the health care request and the plurality of medical providers, the intermediary not being a person treating the patient and the intermediary having access to a processor that is coupled to a database system, and the method comprising the steps performed in the intermediary of:

receiving the health care request from a source thereof in a patient interface provided by the processor;

selecting a subset of medical providers having expertise in treating the medical symptom from a plurality of medical providers;

augmenting, by a medically trained individual, the health care request with medical information that is associated with the medical symptom, is medically relevant to dealing with the medical symptom, and is located by the medically trained individual in the database system using an augmentation interface provided by the processor;

providing the augmented health care request to the subset of medical providers using a provider interface provided by the processor;

receiving one or more treatment proposals for treating the medical symptom from the subset of medical providers in response to the augmented health care request via the provider interface; and providing one or more of the treatment proposals to the source via the patient interface.

2. The method of claim 1 wherein the step of providing the treatment proposals comprises the steps of:

providing each treatment proposal to each medical provider of the subset to enable modifications by each medical provider;

receiving a further treatment proposal from each medical provider of the subset, and providing each of the further treatment proposals to the source.

3. The method of claim 2 further comprising:

having a limited time period during which the treatment proposals may be received from the medical providers of the subset.

4. The method of claim 1 wherein:

the source of the health care request may be one of the patient, the patient's employer, a physician treating the patient, or a payer organization.

5. The method of claim 1 further comprising the step of:
providing a comparative report of each received treatment proposal to the source.

6. The method of claim 1 wherein:
the first criteria further comprises one of insurance coverage, other means of payment, or a specified level of complexity of treatment of the medical symptom.

7. The method of claim 1 further comprising the step of:
selecting the subset of medical providers based on at least one of cost, medical experience, experience treating the medical symptom, amount of expertise related to the medical symptom, amount of education, or reputation.

8. The method of claim 1 further comprising:
using a large scale communications network to communicate at least one of the health care request, the treatment proposal, or the comparative report.

9. The method of claim 8 wherein:
the large scale communications network is a secure large scale communications network.

10. The method of claim 1 wherein the step of augmenting the health care request comprises the step of:
analytically developing the medical information based on the health care request.

11. A method of managing a health care request for a patient, the health care request having a first criteria that is a medical symptom for the patient, the health care request being made to an intermediary between a source of the health care request and the plurality of medical providers, the intermediary not being a person treating the patient and the intermediary having access to a processor that is coupled to a database system, and
the method comprising the steps practiced in the intermediary of:
receiving the health care request from a source thereof in a patient interface provided by the processor;
selecting a subset of medical providers having expertise in treating the medical symptom from a plurality of medical providers;
augmenting, by a medically trained individual, the health care request with medical information associated with the medical symptom, the medical information being medically relevant to dealing with the medical symptom and being located by the medically trained individual in the database system using an augmentation interface provided by the processor;
providing the health care request to the subset of medical providers using a provider interface provided by the processor;
receiving a treatment proposal for the medical symptom from at least one of the medical providers via the provider interface;
providing a comparative report of the treatment proposals to each medical provider via the provider interface;
receiving a final treatment proposal from each medical provider via the provider interface;
providing each final treatment proposal to the source via the patient interface; and
receiving a selection of one of the final treatment proposals associated with at least one of the medical providers from the source via the patient interface.

12. The method of claim 11 further comprising:
informing one of the medical providers of the selection of its treatment proposal.

13. A health care management system comprising:
a patient-client interface for receiving a health care request for a patient having a medical symptom;
a provider-client interface for receiving a treatment proposal for the patient from a medical provider having expertise in treating the medical symptom;
an augmentation interface for receiving an augmentation to the healthcare request from a medically trained individual and
a server in communication with the provider-client interface for receiving the treatment proposal and in communication with the patient-client interface for receiving the health care request for the patient, the server receiving the augmentation from the augmentation interface, communicating the augmentation and the health care request to the provider-client interface, communicating the treatment proposal to the patient-client interface, and receiving a selection of a treatment proposal from the patient-client interface.

14. The health care management system of claim 13 further comprising:
a secure large scale communication network between the patient-client interface and the server.

15. The health care management system of claim 13 further comprising:
a secure large scale communication network between the server and the provider-client interface.

16. The health care management system of claim 13 further comprising:
a database to provide information for the augmentation to the medically-trained individual.

17. A method of responding to a health care request for a patient that describes a medical symptom, the health care request being made to an intermediary between a source of the health care request and a set of one or more medical providers, the intermediary not being a person treating the patient and the intermediary having access to a processor that is coupled to a database system, and
the method comprising the steps performed in the intermediary of:
receiving the health care request from the source thereof in a patient interface provided by the processor;
augmenting the health care request with information that is obtained by a medically trained person, is medically relevant to dealing with the medical symptom, and is located by the medically trained individual in the database system using an augmentation interface provided by the processor; and
providing the augmented health care request to a subset of the medical providers selected by the medically trained person using a provider interface provided by the processor.

18. The method set forth in claim 17 further comprising the steps of:
receiving one or more treatment proposals for treating the medical symptom from the subset of medical providers in response to the augmented health care request; and
providing information concerning the treatment proposals to the source of the health care request.

19. The method set forth in claim 18 wherein the step of providing information comprises:
providing a report concerning the treatment proposals that is made by the medically trained person to the source of the health care request.

20. The method set forth in claim 18 further comprising the steps of:
receiving a selection of a medical provider's treatment proposal from the source of the health care request; and
indicating the selection to the medical provider whose treatment proposal was selected.

* * * * *